(12) United States Patent
Arii et al.

(10) Patent No.: US 9,691,594 B2
(45) Date of Patent: Jun. 27, 2017

(54) METHOD FOR ANALYSIS OF SAMPLE AND APPARATUS THEREFOR

(71) Applicant: RIGAKU CORPORATION, Akishima-shi, Tokyo (JP)

(72) Inventors: Tadashi Arii, Tokyo (JP); Koichi Matsushima, Tokyo (JP); Satoshi Otake, Tokyo (JP)

(73) Assignee: RIGAKU CORPORATION, Akishima-shi (JP)

( * ) Notice: Subject to any disclaimer, the term of this patent is extended or adjusted under 35 U.S.C. 154(b) by 0 days.

(21) Appl. No.: 14/890,512

(22) PCT Filed: Jun. 27, 2014

(86) PCT No.: PCT/JP2014/067103
§ 371 (c)(1),
(2) Date: Nov. 11, 2015

(87) PCT Pub. No.: WO2015/022815
PCT Pub. Date: Feb. 19, 2015

(65) Prior Publication Data
US 2016/0189944 A1    Jun. 30, 2016

(30) Foreign Application Priority Data

Aug. 14, 2013 (JP) ................................. 2013-168470

(51) Int. Cl.
*H01J 49/00* (2006.01)
*H01J 49/04* (2006.01)
(Continued)

(52) U.S. Cl.
CPC ............ *H01J 49/0081* (2013.01); *G01N 5/04* (2013.01); *G01N 25/20* (2013.01); *H01J 49/004* (2013.01);
(Continued)

(58) Field of Classification Search
None
See application file for complete search history.

(56) References Cited

U.S. PATENT DOCUMENTS 5,381,006 A * 1/1995 Wells ................... H01J 49/005
250/282
2009/0008571 A1  1/2009 Matsuura et al.
2009/0026362 A1  1/2009 Arii et al.

FOREIGN PATENT DOCUMENTS

JP    2007-248333 A    9/2007
JP    2007-250450 A    9/2007

OTHER PUBLICATIONS

International Search Report dated Oct. 14, 2014, issued in counterpart Application No. PCT/JP2014/067103 (1 page).
(Continued)

*Primary Examiner* — Jack Berman
(74) *Attorney, Agent, or Firm* — Westerman, Hattori, Daniels & Adrian, LLP

(57) ABSTRACT

A thermal analysis step, a molecule ionization step and a molecular structure analysis step are executed in parallel to a temperature increasing step. In the molecule ionization step, component molecules contained in gas evolved from a sample S due to temperature increase are ionized, and in the molecular structure analysis step, any selected ion out of molecular ions obtained in the molecule ionization step is dissociated to generate fragment ions corresponding to the structural factors of the molecule, and the structure of the molecule is analyzed on the basis of the fragment ions.

5 Claims, 14 Drawing Sheets

(51) Int. Cl.
  *H01J 49/16* (2006.01)
  *G01N 5/04* (2006.01)
  *G01N 25/20* (2006.01)

(52) U.S. Cl.
  CPC ........ *H01J 49/0059* (2013.01); *H01J 49/049* (2013.01); *H01J 49/161* (2013.01); *H01J 49/162* (2013.01)

(56) References Cited

OTHER PUBLICATIONS

Arii, "Development of a Simultaneous Thermogravimetry-Differential Thermal Analysis and Photoionization Mass Spectroscopy Instrument Connected with a Skimmer-Type Interface", The Japan Society of Calorimetry and Thermal Analysis, Tokyo Japan, "Netsu Sokutei (Calorimetry and thermal analysis)", 2011, vol. 38, No. 5, p. 149-p. 156, cited in the specification (8 pages).

Prime et al. "Thermogravimetric Analyzer/Atmospheric Pressure Chemical Ionization Tandem Triple Quadrupole Mass Spectrometer System for Evolved Gas Analysis", Anal. Chem., 1989, vol. 61, No. 11, pp. 1195-1201, cited in ISR (7 pages).

* cited by examiner

METHOD FOR ANALYSIS OF SAMPLE AND APPARATUS THEREFOR

TECHNICAL FIELD

The present invention relates to a method for analysis of sample that increases the temperature of a sample according to a predetermined temperature increasing program, performs a thermal analysis on the sample, and analyses gas evolved from the sample, and a sample analysis apparatus that performs the method.

BACKGROUND ART

A prior art of this type sample analysis apparatus has been made public in an academic journal of Japan Society of Calorimetry and Thermal Analysis by one of the inventors of this application (see Non-patent Document 1). This applicant has already proposed a gas analysis apparatus disclosed in Patent Document 1 as a gas analysis apparatus which is suitably applicable to the above type sample analysis apparatus.

The apparatus disclosed in the Non-patent Document is designed to have a system configuration in which thermogravimetry and differential thermal analysis for a sample and mass spectrometry of gas evolved from the sample can be simultaneously performed. Particularly, a photoionization method (PI method: photoionization method) disclosed in the Patent Document 1 is adopted for the mass spectrometry of gas. The photoionization method is an ionization method utilizing a phenomenon that upon application of light to a molecule, the molecule releases a photoelectron to be ionized when the photon energy of the light is larger than the ionization energy of the molecule.

A mass spectrometry method based on an electron ionization method (EI method: Electron ionization method) that irradiates gas with an accelerated electron beam to dissociate component molecules contained in the gas and generate fragment ions has been known as an analysis method of gas evolved from a sample. According to this electron ionization method, fragment ions corresponding to all the structural factors of the component molecules contained in the gas are generated, and thus this method is suitable for investigation of the structural factors of the component molecules. However, as the number of the component molecules contained in the gas increases, the fragment ions corresponding to the structural factors of the respective component molecules are overlapped with one another. Therefore, there is a drawback that it is difficult to separate and discriminate those component molecules from one another.

On the other hand, according to the mass spectrometry method utilizing the photoionization method proposed by the inventor in the Non-patent Document 1 and the Patent Document 1, component molecules themselves contained in gas are ionized without being dissociated, the component molecules are separated every molecular weight on the basis of obtained molecular ion information, and the molecular weights of the separated component molecules are determined.

However, in the mass spectrometry method utilizing the photoionization method, fragment ions corresponding to the structural factors of the respective component molecules cannot be obtained, and thus it is impossible to perform the structural analysis of the respective component molecules contained in gas. Accordingly, it is impossible to perform qualitative analysis of identifying component molecules of a sample to which it is unknown what component molecules are contained.

According to an apparatus (GC-MS) for separating gas evolved from a sample into component molecules by using a gas chromatography and per forming mass spectrometry, qualitative analysis of the separated component molecules can be also performed. However, in this apparatus, the gas is temporarily cooled and captured, and then re-heated to perform mass spectrometry. Therefore, it is impossible to simultaneously perform thermal analysis and gas analysis in parallel, and also there is a risk that the gas is degenerated in the cooling and re-heating steps.

PRIOR ART DOCUMENTS

Patent Documents

Patent Document 1: JP-2007-248333
Patent Document 2: JP-A-2007-250450

Non-Patent Document

Non-patent Document 1: "Development of a Simultaneous Thermogravimetry-Differential Thermal Analysis and Photoionization Mass Spectroscopy Instrument Connected with a Skimmer-Type interface" Netsu Sokutei 38(5) 2011, P 149-P 156.

DISCLOSURE OF THE INVENTION

Problem to be Solved by the Invention

The present invention has been implemented in view of the foregoing situation, and has an object to obtain thermal analysis data of a sample while the temperature of the sample is increased according to a predetermined temperature increasing program, and separate component molecules contained in gas evolved from the sample to obtain structure analysis data of the separated molecules in parallel.

Means of Solving the Problem

A sample analysis method according to the present invention is characterized by comprising a temperature increasing step, a thermal analysis step, a molecule ionization step, and a molecular structure analysis step, wherein the thermal analysis step, the molecule ionization step and the molecular structure analysis step are executed in parallel to the temperature increasing step.

In the temperature increasing step, the temperature of the sample is increased according to a predetermined temperature increasing program. In the thermal analysis step, thermal analysis is performed on the sample. In the molecule ionization step, component molecules contained in gas evolved from the sample due to the temperature increase are ionized. In the molecular structure analysis step, any selected ion out of molecular ions obtained in the molecule ionization step is dissociated to generate fragment ions corresponding to the structural factors of the molecule, and the structure of the molecule is analyzed on the basis of the fragment ions.

According to this method, thermal analysis data of the sample can be obtained while the temperature of the sample is increased according to a predetermined temperature increasing program. In addition, the component molecules contained in the gas evolved from the sample are separated and the structure analysis data of the separated molecules can be obtained in parallel.

Here, the thermal analysis step is executed on the sample disposed in a sample chamber. Gas which is evolved from the sample due to the temperature increase is fed into an analysis chamber by a skimmer-type gas introducing interface, and the molecule ionization step and the molecular structure analysis step are executed in the analysis chamber.

The skimmer-type gas introducing interface is a gas introducing interface having a double tube structure comprising an inner tube and an outer tube which is coaxially provided around the inner tube. The skimmer-type gas introducing interface is configured so that one end opening of the outer tube is made to intercommunicate with the sample chamber, the other end opening of the inner tube is made to intercommunicate with the analysis chamber, the pressure at the sample chamber side is set to be higher than that at the analysis chamber to form a pressure difference between the chambers, and the pressure of the intermediate space between the outer tube and the inner tube is set to an intermediate pressure between the respective chambers, thereby having a function of rapidly feeding the as evolved in the sample chamber to the analysis chamber with the pressure difference.

The sample chamber and the analysis chamber are connected to each other through the skimmer-type gas introducing interface, whereby the distance between both the chambers can be set to a very short distance. Therefore, a loss caused by the feeding of the evolved gas can be nullified, and the molecular structure analysis of the evolved gas can be performed efficiently with high precision. In addition, space saving of the facilities can be performed.

It is preferable to execute the molecule ionization step and the molecular structure analysis step by using an ion trap mass spectrometry instrument. The ion trap mass spectrometry instrument is a mass spectrometry instrument which is configured so as to temporarily capture the generated ions and then perform mass separation. By using the ion trap mass spectrometry instrument, it is possible to dissociate a specific ion after the ion is captured (trapped) and detect generated fragment ions. By using this ion trap mass spectrometry instrument, any selected ion out of molecular ions obtained in the molecule ionization step is captured, the captured ion is dissociated to generate fragment ions corresponding to the structural factors of the molecule, and the structure of the molecule can be analyzed on the basis of the fragment ions.

In the molecule ionization step, the component molecules contained in the gas evolved from the sample are preferably irradiated with light to ionize the molecules. That is, the molecule ionization step is executed by using a mass spectrometry method based on a photoionization method (PI method). Accordingly, the dissociation of the component molecular ions can be suppressed, and the ions can be easily separated every component molecule. Particularly, in the present invention, it is preferable to ionize the molecules with vacuum ultraviolet light having lower directivity than a laser beam. Accordingly, the molecules can be ionized in a broader area as compared with the laser beam.

Furthermore, in the present invention, the thermal analysis data obtained in the thermal analysis step and the data obtained in the molecular structure analysis step are preferably displayed on the same graph with the temperature set as a common variable. More specifically, the mass variation caused by the temperature increase of the sample in the thermal analysis step is analyzed and displayed on a graph, and with respect to the data obtained in the molecular structure analysis step, thermograms of the respective generated fragment ions are displayed on the same graph as the mass variation.

As described above, by displaying the respective analysis data on the same graph, identification analysis can be performed while the behavior of evolution of the qualitatively analyzed gas components and the correlation of the thermal analysis curve can be clearly separated.

Next, the sample analysis apparatus according to the present invention is an apparatus for performing the above sample analysis method, and has a sample chamber, a thermal analyzer, a skimmer-type gas introducing interface, a gas analyzer and a control/processing device.

The sample is disposed in the sample chamber. The thermal analyzer increases the temperature of the sample according to a predetermined temperature increasing program, and performs thermal analysis on the sample. The skimmer-type gas introducing interface feeds, to the analysis chamber, gas evolved from the sample disposed in the sample chamber due to the temperature increase.

The gas analyzer ionizes the component molecules contained in the gas fed to the analysis chamber, and dissociates any selected ion out of molecular ions obtained by the ionization to generate fragment ions, and analyzes the structure of the molecule on the basis of the fragment ions.

The control/processing device controls the thermal analyzer and the gas analyzer to execute the thermal analysis step, the molecule ionization step and the molecular structure analysis step in parallel to the temperature increasing step, and processes thermal analysis data obtained by the thermal analyzer and gas analysis data obtained by the gas analyzer.

The sample analysis method of the present invention is properly performed by using the sample analysis apparatus having the above construction, and the thermal analysis data of the sample can be obtained while the temperature of the sample is increased according to a predetermined temperature increasing program. Furthermore, in parallel to this process, the component molecules contained in the gas evolved from the sample are separated, and the structural analysis data of the separated molecules can be obtained.

Here, it is preferable to apply an ion trap mass spectrometry instrument as the gas analyzer. According to the ion trap mass spectrometry instrument, the component molecules contained in the gas fed to the analysis chamber are ionized, and any selected ion out of the molecular ions obtained by the ionization can be captured. Then, the captured for is dissociated to generate fragment ions, and the structure of the molecule can be analyzed on the basis of the fragment ions.

Furthermore, the gas analyzer is preferably configured to irradiate the component molecules contained in the gas evolved from the sample with light to ionize the molecules. Accordingly, the dissociation of the component molecular ions can be suppressed, and the ions can be easily separated every component molecule. Particularly, by using a light source for irradiating vacuum ultraviolet light having lower directivity than a laser beam, molecules can be ionized in a broader area as compared with the laser beam.

Furthermore, it is preferable that the control/processing device displays the thermal analysis data obtained by the thermal analyzer and the gas analysis data obtained by the gas analyzer on the same graph with the temperature set as a common variable, and outputs the thermal analysis data and the gas analysis data. Specifically, the mass variation caused by the temperature increase of the sample is analyzed by the thermal analyzer, and the control/processing device displays the mass variation caused by the temperature increase of the sample as the thermal analysis data on the graph. Furthermore, the control/processing device displays thermograms of the respective fragment ions generated by the gas analyzer as the gas analysis data on the same graph as the mass variation caused by the temperature increase of the sample.

As described above, according to the present invention, the thermal analysis data of the sample are obtained while the temperature of the sample is increased according to a predetermined temperature increasing program, and in parallel to the above step, the component molecules contained in the gas evolved from the sample can be separated and the structure analysis data of the separated molecules can be obtained.

DESCRIPTION OF REFERENCE NUMERALS

S: sample, 10: casing, 11: sample chamber, 12: exhaust pipe, 20: thermal analyzer, 21: thermal analyzer main body, 22: gas supply source; 23: heating furnace, 24: detector, 30: gas analyzer, 31: analysis chamber, 31A: ionization unit, 313: ion trap portion, 32: gas analyzer main body, 33: turbo molecular pump, 34: diffusion pump, 35: ion gauge, 36: ion detector, 37: light source, 40: gas feeding device, 41: inner tube, 42: outer tube, 43: intermediate chamber, 44: rotary pump, 50: central control/processing device

BEST MODES FOR CARRYING OUT THE INVENTION

An embodiment of the present invention will be described in detail with reference to the drawings.

Construction of Sample Analysis Apparatus

First, the construction of a sample analysis apparatus according to an embodiment of the present invention will be described.

Figure 1:
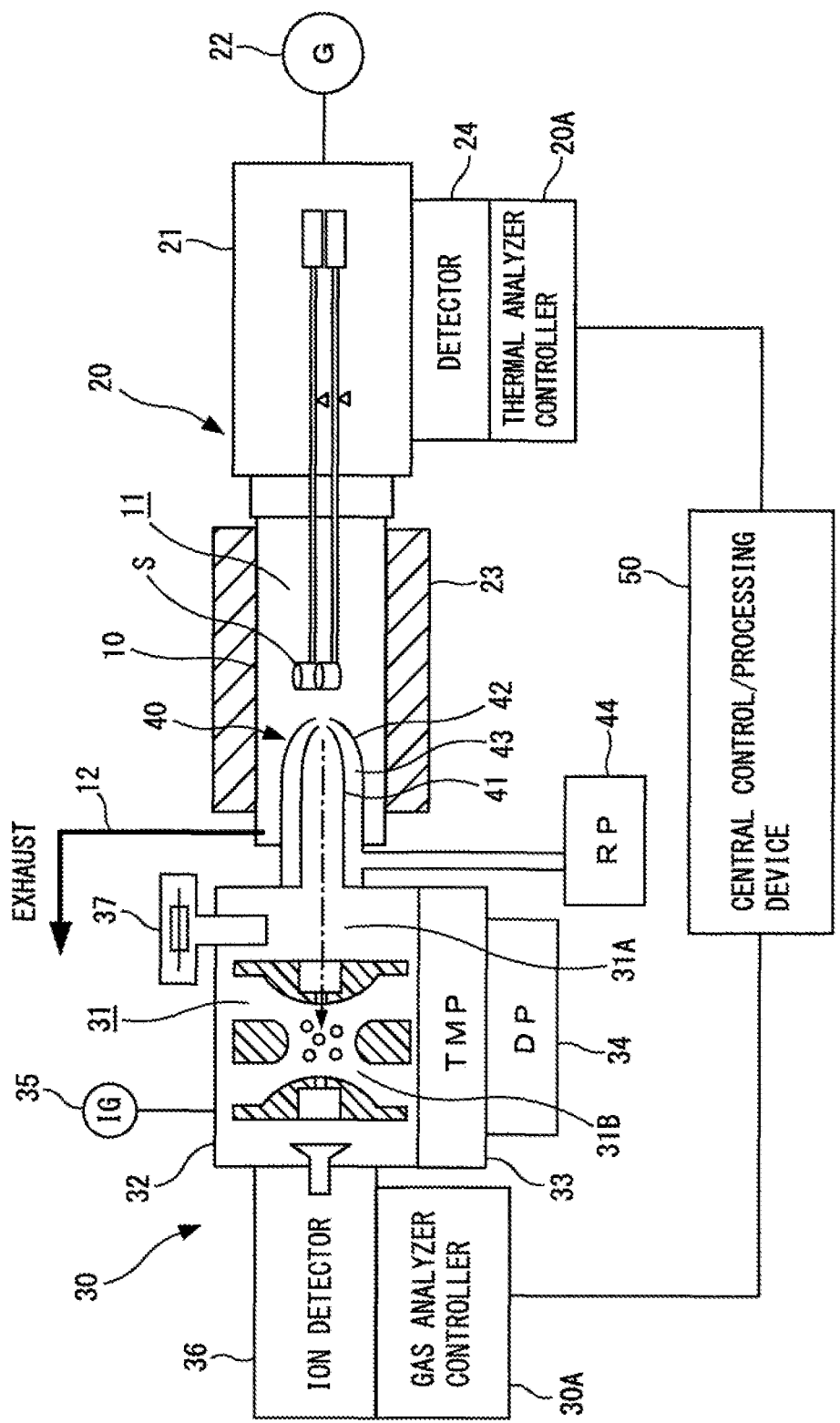
FIG. 1 is a schematic diagram showing a sample analysis apparatus according to an embodiment of the present invention.

As shown in FIG. 1, the sample analysis apparatus according to this embodiment has a sample chamber 11 in which a sample S is disposed, a thermal analyzer 20 for performing the thermal analysis, a gas feeding device 40 for feeding, to an analysis chamber 31, gas evolved from the sample S disposed in the sample chamber 11 due to temperature increase, a gas analyzer 30 for analyzing component molecules contained in the gas fed to the analysis chamber 31, and a central control/processing device 50 for controlling the thermal analyzer 20 and the gas analyzer 30, and processing analysis data obtained in the respective analyzers.

The sample chamber 11 is formed inside a casing 10. One end of the casing 10 is connected to the thermal analyzer main body 21, and carrier gas is supplied from a gas supply source 22 into the thermal analyzer main body 21. The carrier gas flows from the thermal analyzer main body 21 to the casing 10, and extra carrier gas is exhausted through an exhaust pipe 12 connected to the casing 10. Inert gas such as helium (He) or the like is used as the carrier gas.

A heating furnace 23 is provided on the outer periphery of the casing 10. The heating furnace 23 is also a constituent element of the thermal analyzer 20, and controlled by the central control/processing device 50. The central control/processing device 50 controls the heating furnace 23 to increase the temperature of the sample S disposed in the sample chamber 11 according to a predetermined temperature increasing program.

In this embodiment, a TG-DTA thermal analyzer having a function of performing thermogravimetry (TG) and differential thermal analysis (DTA) is applied as the thermal analyzer 20. The thermogravimetry is a thermal analysis method for measuring the mass of sample S as a function of temperature while the temperature of the sample S is varied according to a predetermined program. A thermobalance is used for the thermogravimetry (TG) The differential thermal analysis (DTA) is a thermal analysis method of detecting, as a temperature difference from a reference material (Reference), a thermal variation occurring in the sample S due to physical variation or chemical variation occurring when the sample S is heated or cooled. The temperature difference from the reference material is detected by a thermocouple welded to a heat-sensitive plate of a sample holder.

Analysis data such as thermogravimetric data, the differential thermal analysis data, etc. which are obtained by the thermal analyzer 20 are fed from the detector 24 provided to the thermal analyzer to the central control/processing device 50.

The analysis chamber 31 is formed inside the gas analyzer main body 32. A turbo molecular pump 33 and a diffusion pump 34 are equipped to the as analyzer main body 32. The diffusion pump 34 roughly reduces the internal pressure of the analysis chamber 31, and the turbo molecular pump 33 further reduces the internal pressure of the analysis chamber 31 roughly reduced by the diffusion pump 34 to a vacuum state or a pressure-reduced state near to the vacuum state. The pressure in the analysis chamber 31 is detected by an ion gauge 35 as a pressure gauge, and a detection result is fed as an electrical signal to the central control/processing device 50.

A so-called skimmer-type gas introducing interface which is configured to have a differential exhaust structure based on a double tube is used for the gas feeding device 40. That is, the gas feeding device 40 has an inner tube 11 for feeding gas therethrough, an outer tube 42 enveloping the inner tube 41, and a rotary pump 44 for exhausting the intermediate chamber 43 between the outer tube 42 and the inner tube 41.

The gas feeding device 40 sets the outside of the outer tube 42 (that is, the inside of the sample chamber 11) to high pressure, sets the inside of the inner tube 41 (that is, the inside of the analysis chamber 31) to low pressure, and sets the intermediate chamber 43 to an intermediate pressure between the high pressure and the low pressure, whereby the gas feeding device 40 has a function of feeding gas occurring in the sample chamber 11 to the analysis chamber 31 by the inner tube 41 while maintaining the pressure difference between the sample chamber 11 and the analysis chamber 31 which are different in pressure.

End portions of the inner tube. 41 and the outer tube 42 at the sample chamber 11 side are formed as orifices (that is, micropores), and the other end portions thereof at the analysis chamber 31 side which confront the one end portions are formed as openings of normal sizes which have no orifice effect. As described above, the end portions of the inner tube 41 and the outer tube 42 at the sample chamber 11 side are formed as orifices, and the other end portions at the opposite side, that is, at the analysis chamber 31 side are formed as normal openings, whereby gas evolved from the sample S can be efficiently collected and efficiently fed to the analysis chamber 31 by the orifices.

An ion trap mass spectrometry instrument is applied as the gas analyzer 30. Furthermore, the photoionization method (PI method) described above is adopted for ionization of gas fed into the analysis chamber 31. In addition, a constituent element for implementing an electron ionization method (EI method) is also installed, and the gas analyzer 30 is configured so as to be capable of implementing the PI method and the EI method while switching the PI method and the EI method.

An ionization unit 31A and an ion trap portion 31B are equipped in the analysis chamber 31 formed inside the gas analyzer main body 32, and an ion detector 36 is connected to the ion trap portion 31B.

The ionization unit 31A is a constituent unit for ionizing component molecules of gas fed from the sample chamber 11 by the photoionization method. The ionization unit 31A is provided with a light source 37 for irradiating vacuum ultraviolet light, and gas which is fed through the gas feeding device 40 into the analysis chamber 31 is irradiated with light from the light source 37. When the photon energy of the light at that time is larger than the ionization energy of the component molecules contained in the gas, the component molecules emit photoelectrons, and are ionized.

A discharge tube which radiates vacuum ultraviolet light having lower directivity than a laser beam is adopted as the light source 37. For example, a discharge tube disclosed in Patent Document 2 (JP-A-2007-250450) or on paragraph [0074] of Patent Document 1 may be adopted.

Since dissociation of the component molecules contained in the gas fed from the sample chamber 11 can be suppressed by using the photoionization method (PI method) as described above, the component molecules can be directly ionized and subjected to mass spectrometry, whereby ion information of the molecules can be obtained.

Here, the photoionization method (PI method) and the electron ionization method (EI method) will be described in comparison with each other with reference to FIGS. 2 to 6.

Figure 2:
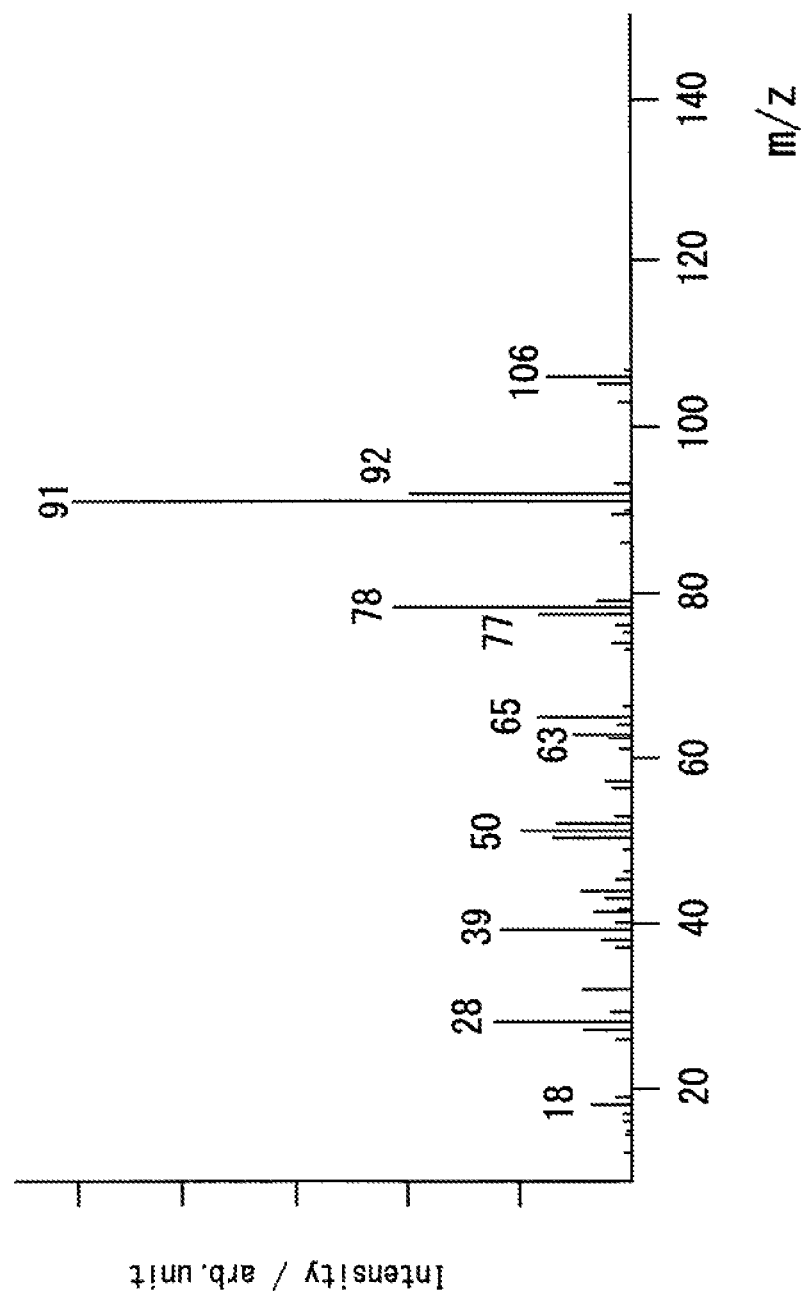
FIG. 2 is a diagram showing an example of mass spectral data obtained by mass spectrometry based on an electron ionization method (EI method).
Figure 3:
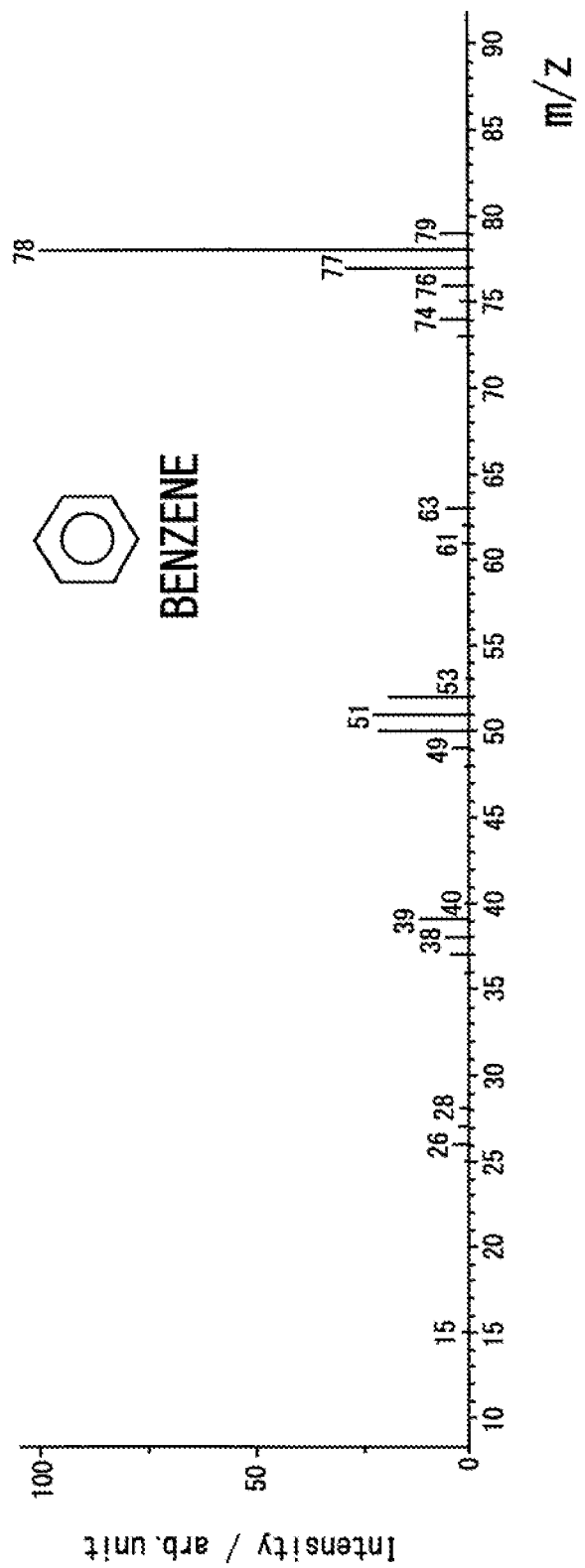
FIG. 3 is a diagram showing mass spectral data of benzene contained in the mass spectral data shown in FIG. 2.
Figure 4:
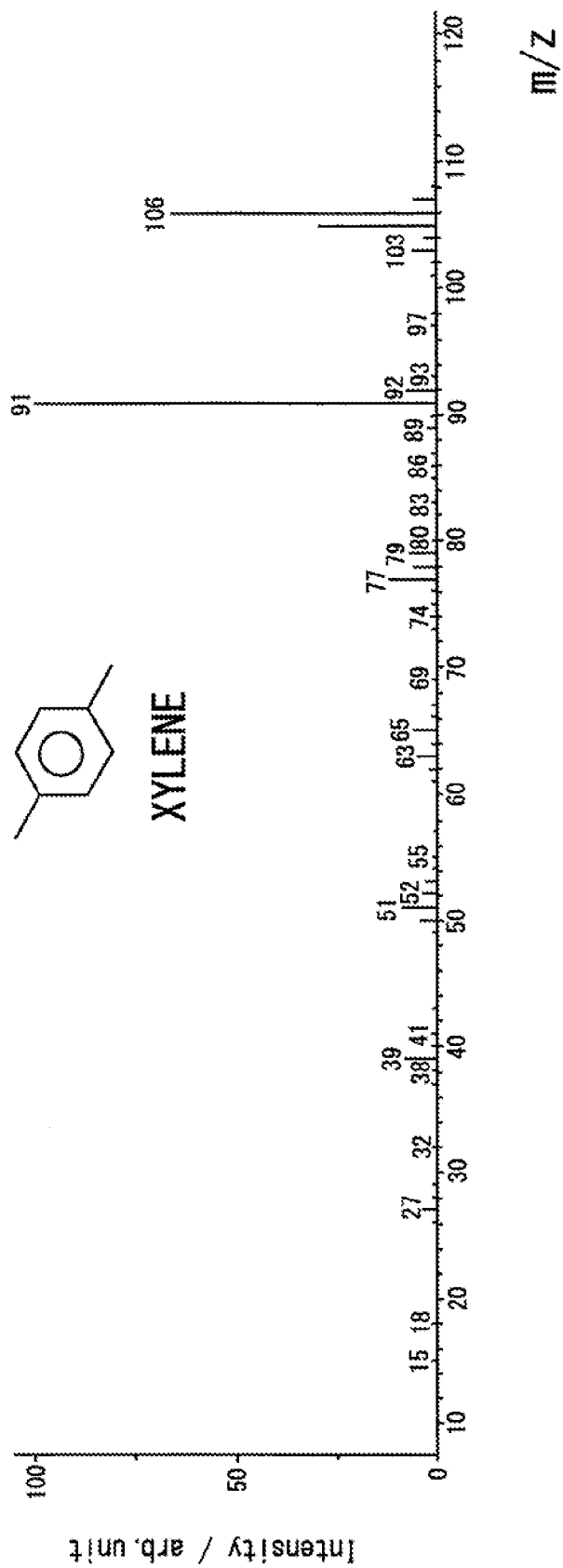
FIG. 4 is a diagram showing mass spectral data of xylene contained in the mass spectral data shown in FIG. 2.
Figure 5:
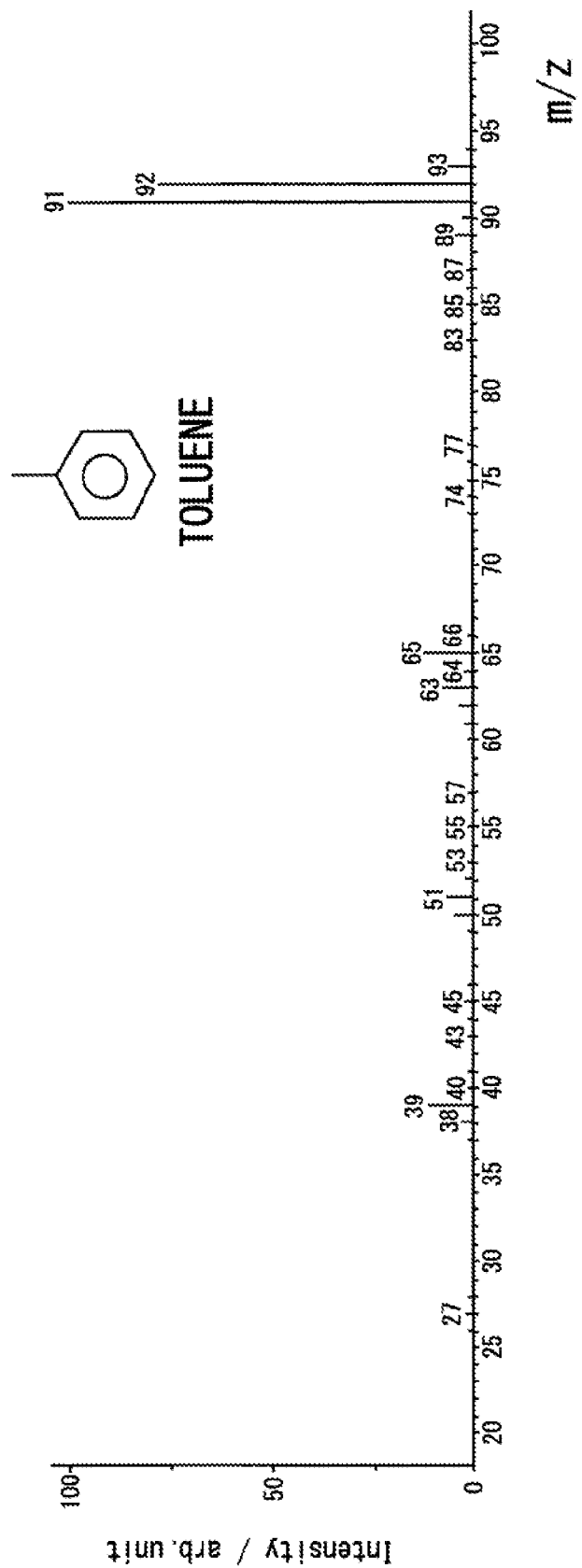
FIG. 5 is a diagram showing mass spectral data of toluene contained in the mass spectral data shown in FIG. 2.

FIG. 2 shows an example of mass spectral data obtained by the mass spectrometry based on the electron ionization method (EI method). The mass spectrum is obtained by separating ions obtained with the mass spectrometry instrument every mass-to-charge ratio (m/z) and recording the separated ions. In the electron ionization method, molecular ions are bombarded with electrons to be dissociated, and fragment ions corresponding to the structural factors of the molecules are generated. That is, mass spectral data of benzene shown in FIG. 3, mass spectral data of xylene shown in FIG. 4 and mass spectral data of toluene shown in FIG. 5 are superimposed on one another, and displayed as mass spectral data as shown in FIG. 2. Accordingly, it is difficult to clearly assort and identify the respective structural factors (benzene, xylene, toluene) of the molecules on the basis of the mass spectral data of FIG. 2.

Figure 6:
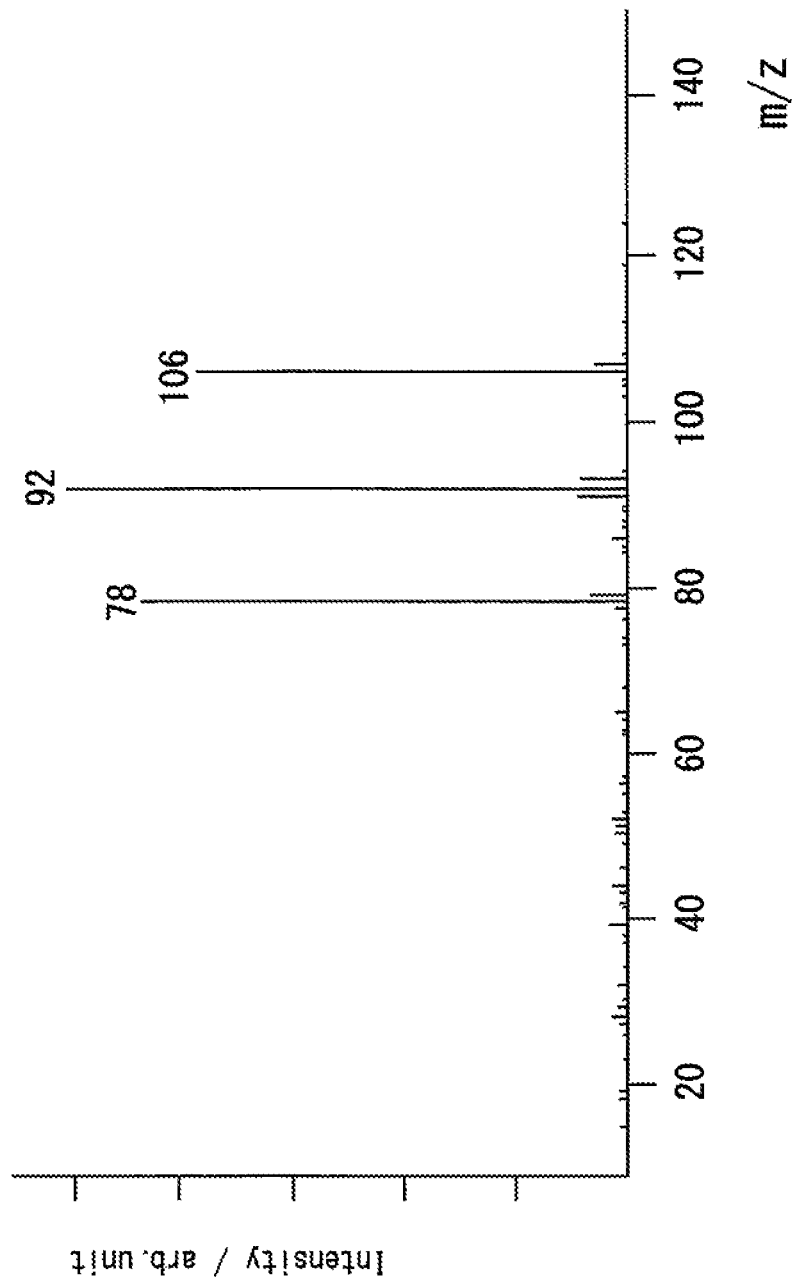
FIG. 6 is a diagram showing an example of mass spectral data obtained by mass spectrometry used on a photoionization method (PI method).

FIG. 6 shows an example of mass spectral data obtained by the mass spectrometry based on the photoionization method (PI method). In the mass spectral data shown in FIG. 6, only the molecular ion information (m/z 78, m/z 52, m/z 106) is clearly shown.

Figure 7:
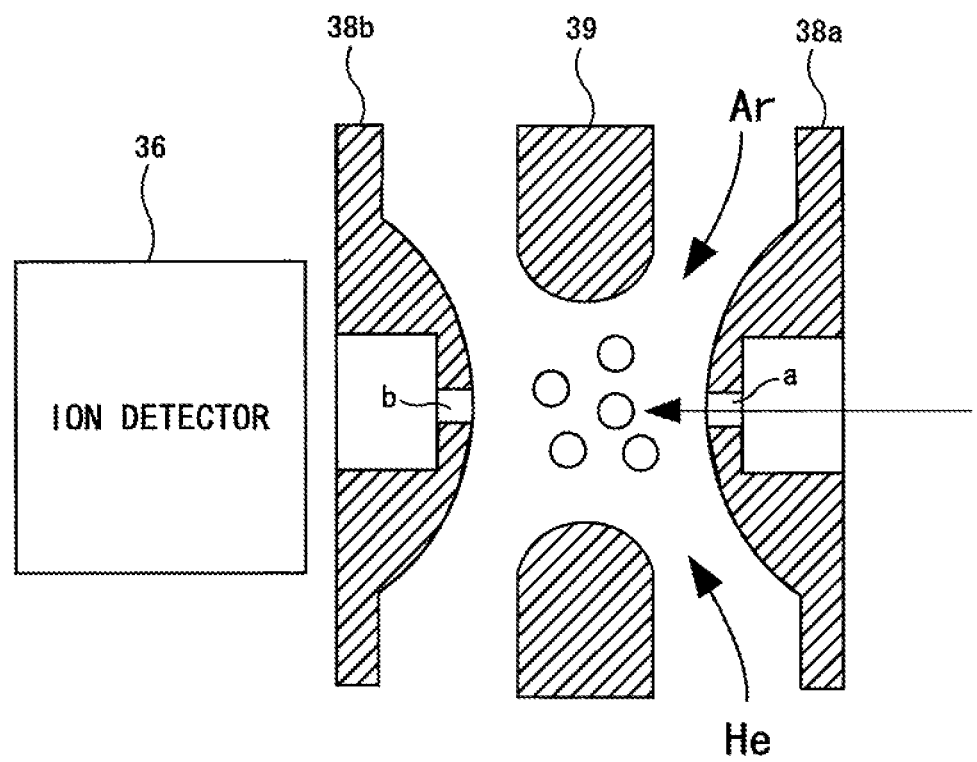
FIG. 7 is a schematic diagram showing the construction of an ion trap portion of a gas analyzer.

End cap electrodes 38a, 38b and a donut-shaped ring electrode 39 as shown in FIG. 7 are equipped at the ion trap portion 31B, and ions are introduced from an ion take-in port "a" provided to the end cap electrode 38a. The introduced ions are captured under a simple harmonic oscillation state in an inner space of the ring electrode 39 by applying a high frequency voltage to the donut-shaped ring electrode 39. Thereafter, the captured ions are led to an ion take-out port "b" and fed out from the ion take-out port "b" to the ion detector 36 by scanning the high frequency voltage.

With respect to the motion of ions when the ions are captured at the ion trap portion 31B, the ions minutely oscillate at a high angular frequency, and also make a slow harmonic oscillation at a lower angular frequency in both of a z-axis direction (an axial direction connecting the centers of the end cap electrodes 38a, 38b) and an r-axis direction (a radial direction of the ring electrode 39). In order to efficiently lead the ions making such a motion to the ion take-out port, it is necessary to reduce the orbit amplitude of the ions. Therefore, helium gas (He) is introduced into the ion trap portion 31B, and the orbit amplitude of ions is reduced by impinging the helium gas against the ions.

An ion having any mass number can be selectively captured at the ion trap portion 31B by adjusting the frequency of the voltage to be applied to the ring electrode 39. Therefore, according to this embodiment, ions which are fed to the ion trap portion 31B are assorted and captured every molecule, and then fed to the ion detector 36.

Collision gas is selectively supplied from a collision gas supply source (not shown) to the ion trap portion 31B. The collision gas has a function of colliding with ions captured at the ion trap portion 31B to dissociate the ions and generate fragment ions of molecules. For example, argon gas (Ar) is used as the collision gas.

In this embodiment, ions which are preset in the central control/processing device 50 are selected, and when the selected ions are captured at the ion trap portion 31B, the collision gas is supplied to dissociate the ions and generate fragment ions of the molecules. The generated fragment ions are subjected to mass spectrometry in the ion detector 36, whereby the structural factors of the molecules can be clarified.

The mass spectrometry is performed on the thus-fed ions by the ion detector 36. The ion detector 36 outputs mass spectral data obtained by separating and recording the molecular ions every mass-to-charge ratio (m/z), and mass spectral data obtained by separating and recording, every mass-to-charge ratio (m/z), fragment ions corresponding to the structural factors obtained by selectively dissociating the molecular ions as mass analysis data associated with the fragment ions.

The thermal analyzer 20 and the gas analyzer 30 are equipped with controllers 20A and 30A respectively, and the controllers 20A and 30A are collectively controlled by the central control/processing device 50. The central control/processing device 50 has a function of receiving analysis data from the detector 24 of the thermal analyzer 20 and the ion detector 36 of the gas analyzer 30, and processing these analysis data in a lump. The central control/processing device 50 is configured to contain a computer, for example. Peripheral equipment such as an output device (for example, a display, a printer), an input device (for example, a keyboard, a mouse), etc. are connected to the central control/processing device 50 through an input/output interface.

Sample Analysis Method

Next, a sample analysis method using the sample analysis apparatus described above will be described.

Figure 8:
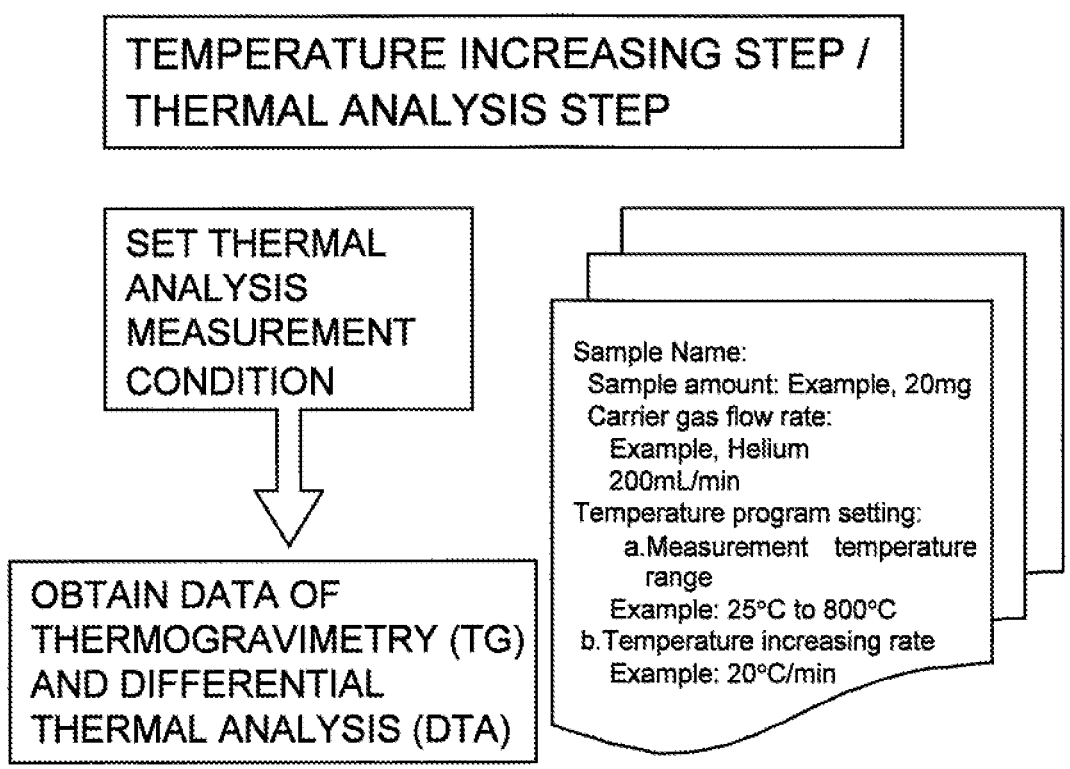
FIG. 8 is a diagram showing a temperature increasing step and a thermal analysis step.
Figure 9:
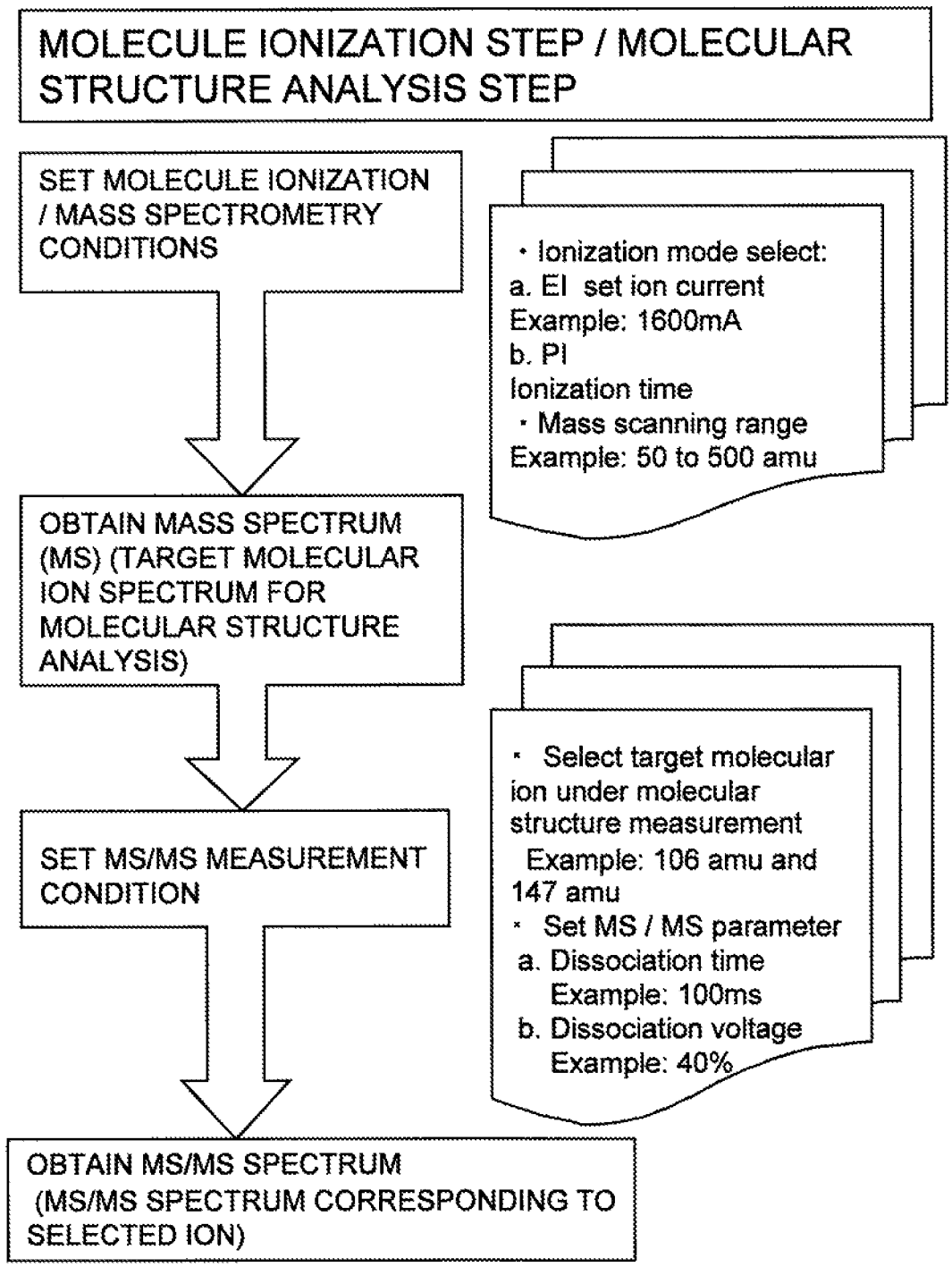
FIG. 9 is a diagram showing a molecule ionization step and a molecular structure analysis step.
Figure 10:
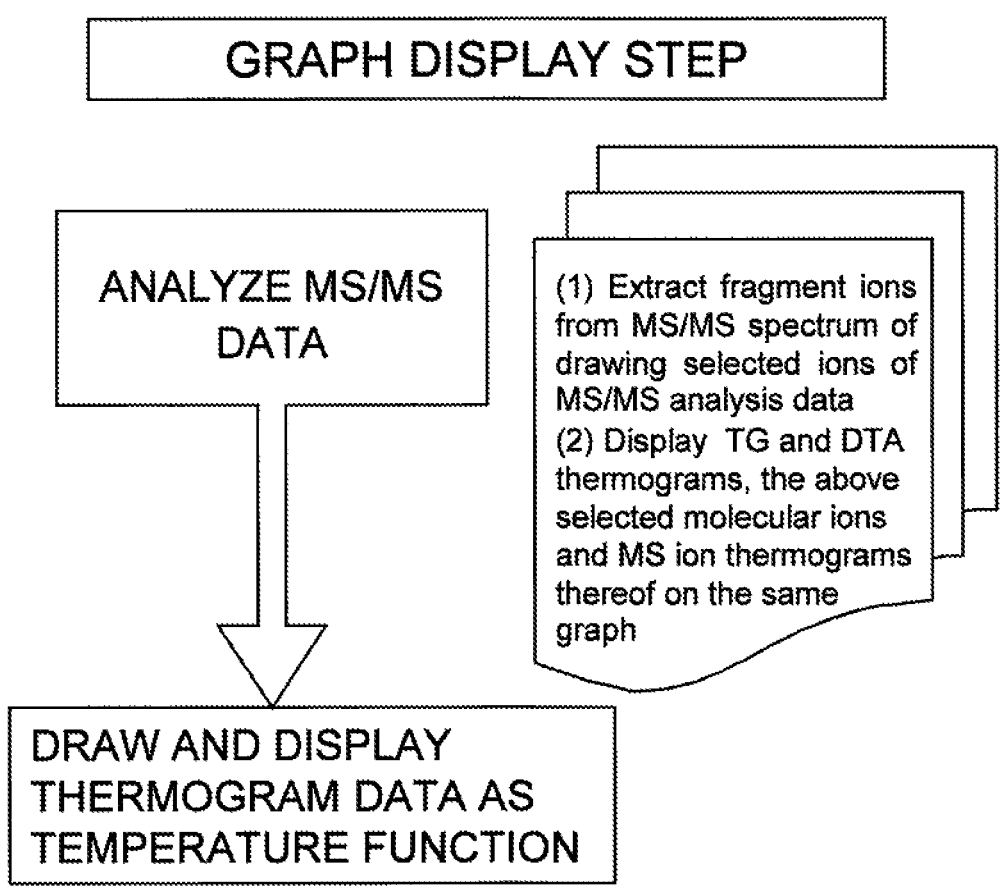
FIG. 10 is a diagram showing a graph display step.

FIGS. 8 to 10 are diagrams showing the respective steps of the sample analysis method.

The sample analysis method according to this embodiment contains a temperature increasing step, a thermal analysis step, a molecule ionization step, and a molecular structure analysis step. The thermal analysis step, the molecule ionization step and the molecular structure analysis step are executed in parallel to the temperature increasing step.

The temperature increasing step is a step of controlling the heating furnace 23 by the central control/processing device 50 so that the temperature of the sample S disposed in the sample chamber 11 is increased according to a predetermined temperature increasing program.

The thermal analysis step is a step of performing thermal analysis by the thermal analyzer 20. In this embodiment, as described above, the thermogravimetry (TG) and the differential thermal analysis (DTA) are performed, and the thermogravimetry data and the differential thermal analysis data are output from the detector 24 to the central control/processing device 50.

As shown in FIG. 8, in order to execute the temperature increasing step and the thermal analysis step, conditions necessary for the thermal analysis measurement such as a sample name, the supply amount of carrier gas to be supplied into the sample chamber 11, a measurement temperature range, a temperature increasing rate, etc. are preset in the central control/processing device 50. On the basis of these preset measurement conditions, the central control/processing device 50 controls the thermal analyzer 20 through the thermal analyzer controller 20A to execute the temperature increasing step and the thermal analysis step, whereby the measurement data of the thermogravimetry (TG) and the differential thermal analysis (DTA) can be obtained.

The molecule ionization step and the molecular structure analysis step are executed by the gas analyzer 30. That is, as which is evolved from the sample S in the sample chamber 11 due to the temperature increase is fed into the ionization unit 31A of the gas analyzer 30 through the gas feeding device 40.

As shown in FIG. 9, in order to execute the molecule ionization step and the molecular structure analysis step, conditions necessary for ionization of component molecules and acquisition of a mass spectrum (MS) of the ionized component molecules such as selection of an ionization mode, a mass scanning range, etc. are preset in the central control/processing device 50. On the basis of these preset conditions, the central control/processing device 50 controls the gas analyzer 30 through the gas analyzer controller 30A to execute the molecule ionization step and the molecular structure analysis step.

The molecule ionization step is executed at the ionization unit 31A. Specifically, the component molecules contained in the gas fed to the ionization unit 31A are irradiated with light from the light source 37 to ionize the component molecules on the basis of the principle of the photoionization method (PI method).

The molecular structure analysis step is executed at the ion trap portion 31B and the ion detector 36. That is the ions of the component molecules obtained by the ionization unit 31A are assorted and captured every molecule at the ion trap portion 31B, and fed to the ion detector 36. Then, in the ion detector 36, the molecular ions are separated every mass-to-charge ratio (m/z) to create mass spectral data (MS), and the mass spectral data are output to the central control/processing device 50.

Furthermore, as shown in FIG. 9, in the central control/processing device 50 are preset conditions necessary to obtain the mass spectrum (MS/MS) of a further selected molecular ion from the mass spectrum (MS) of ionized component molecules, such as selection of the molecular ion as a molecular structure analysis target, setting of MS/MS parameters, etc.

The gas analyzer 30 selects ions of a preset mass-to-charge ratio (m/z), and captures the selected ions at the ion trap portion 31B. Then the collision as is supplied to dissociate the ions and generate fragment ions of the molecules. The thus-generated fragment ions are subjected to mass spectrometry in the ion detector 36, and the mass spectral data (MS/MS) corresponding to the structural factors of the molecules are created and output to the central control/processing device 50.

A processing step of creating the mass spectral data (MS) associated with these molecular ions and a processing step of dissociating the molecular ions and further creating the mass spectral data (MS/MS) corresponding to the structural factors of the molecules are contained in the molecular structure analysis step.

Figure 11:
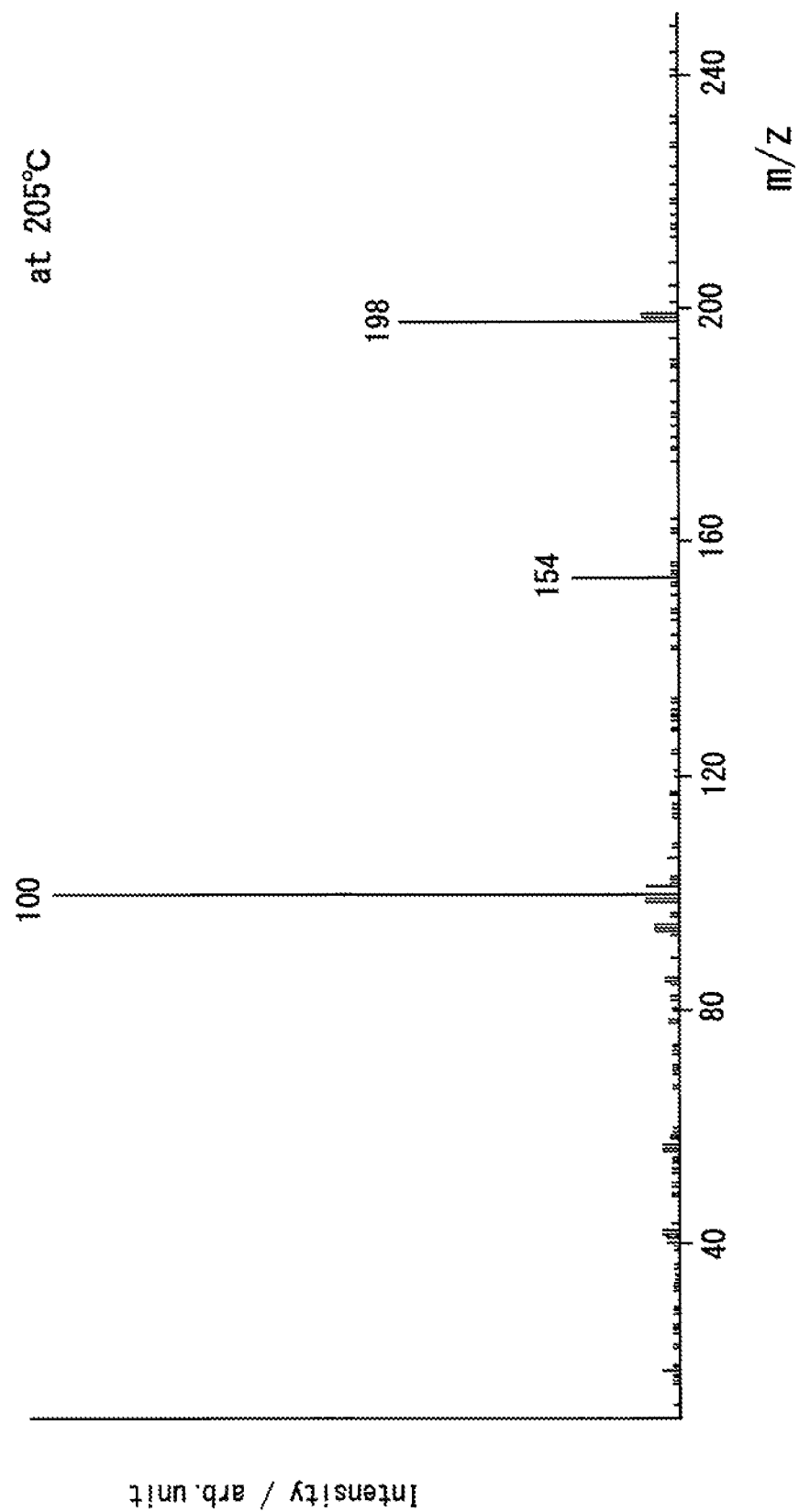
FIG. 11 is a diagram showing a specific example of mass spectral data of molecular ions obtained in the molecule ionization step.

FIG. 11 shows a specific example of the mass spectral data (MO) associated with the molecular ions obtained in the molecule ionization step. The mass spectral data shown in FIG. 11 are associated with molecular ions contained in gas evolved when the temperature of polymethylmethacrylate is increased to 205° C., and m/z 198, 154, 100 are clearly shown as characteristic ions.

Figure 12:
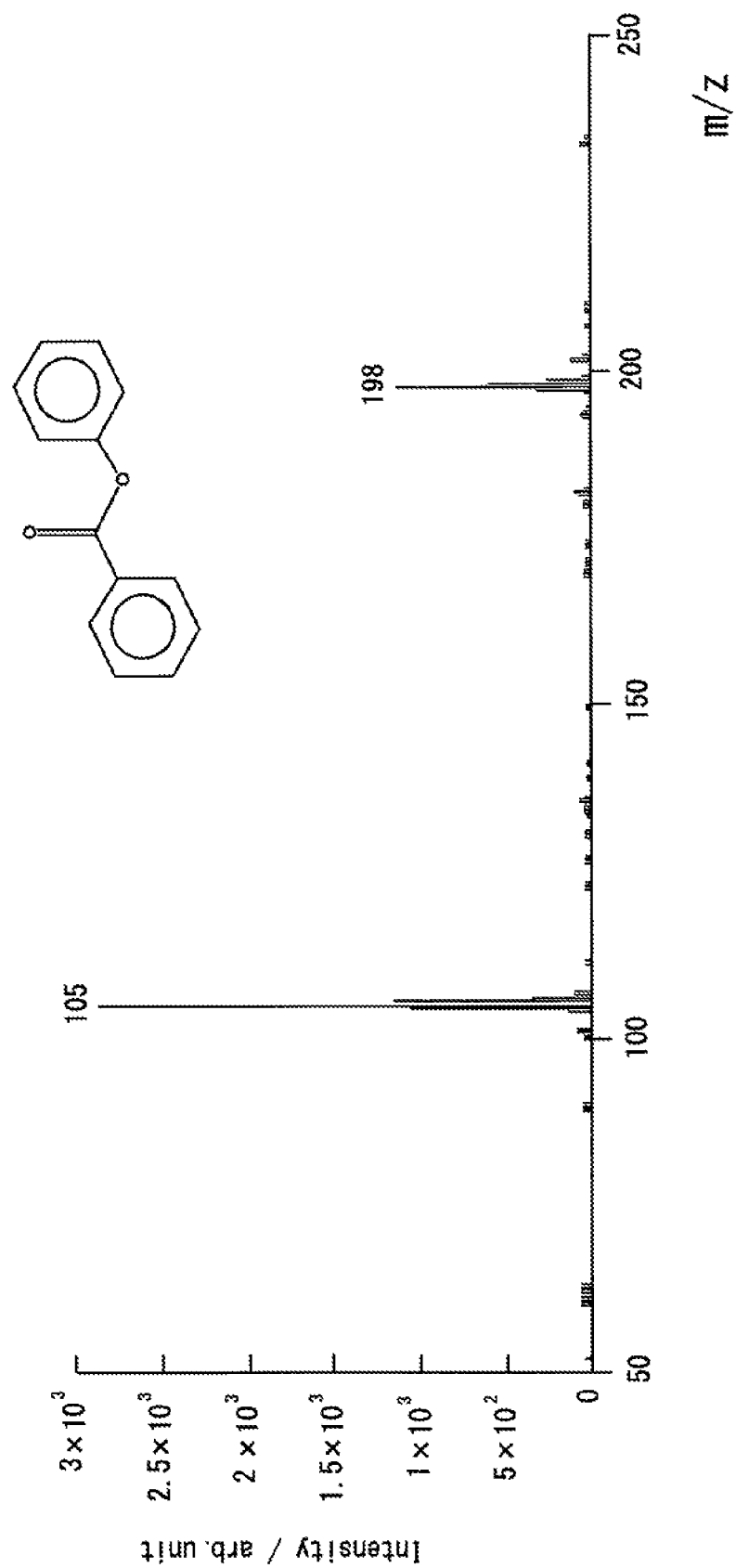
FIG. 12 shows mass spectral data of fragment ions obtained by dissociating ions of m/z 198 at the ion trap portion.

FIG. 12 shows the mass spectral data (MS/MS) obtained by selecting the characteristic ions of m/z 198 shown in FIG. 11, capturing these ions at the ion trap portion 31B, bombarding the ions with collision gas to dissociate the ions and generate fragment ions, and performing the mass spectrometry on the respective fragment ions with the ion detector 36. Information on not only the ions of m/z 198, but also the fragment ions of m/z 105 appears in this mass spectral data, and this ion information corresponds to the structural factors of the molecules.

Therefore, the structural factors of molecules contained in evolved gas can be identified and qualitatively analyzed from the mass spectral data of FIG. 12 by using an existing library for specifying the relationship between the mass spectral data and the molecular structure. For example, a library supplied by National Institute of Standards and Technology (NIST: National Institute of Standards and Technology) is known as the existing library. As a result of the qualitative analysis using this library based on the mass spectral data of FIG. 9, the molecular structure is identified as Phenyl benzenoate (Phenyl benzenoate).

Figure 13:
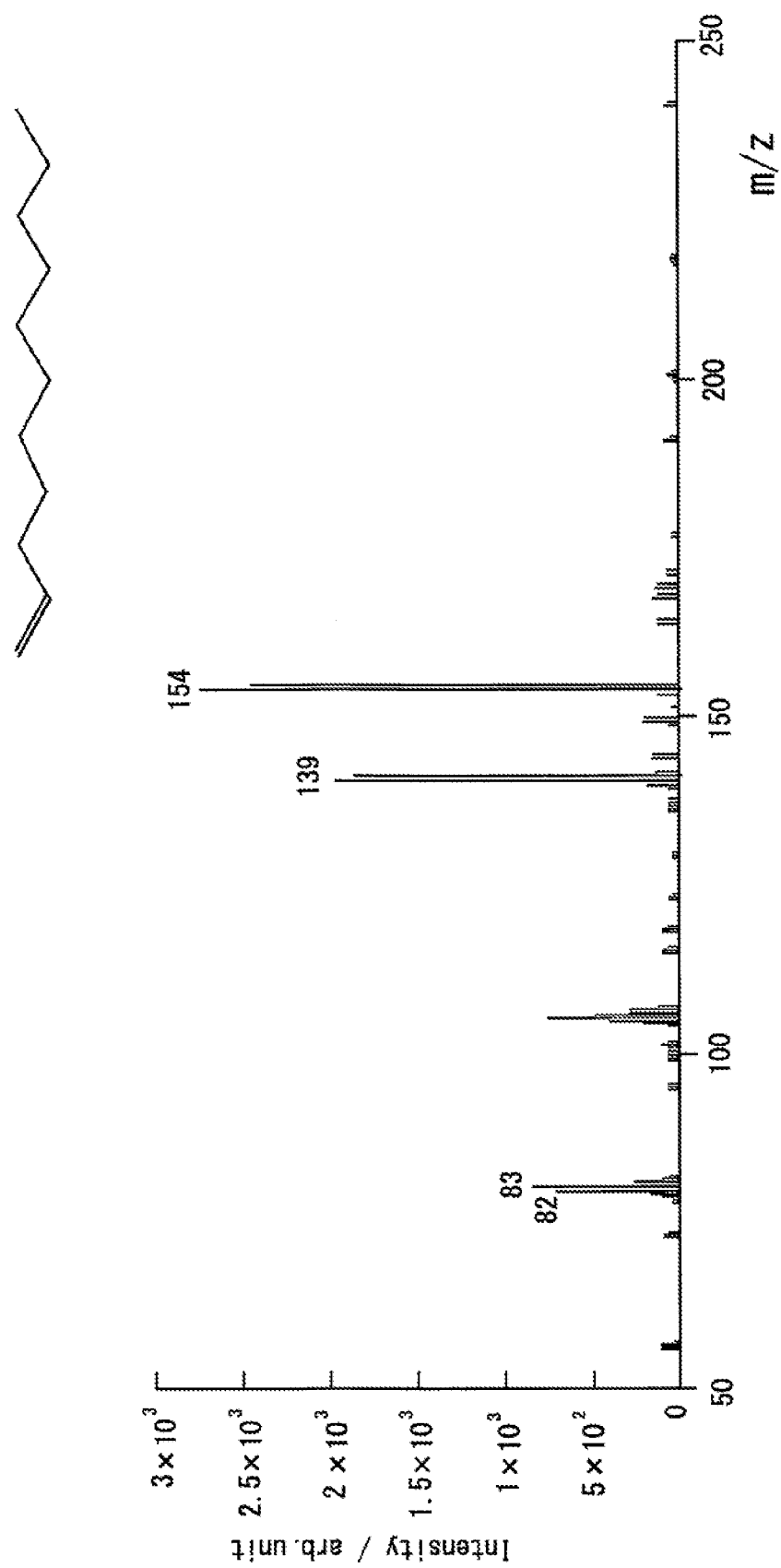
FIG. 13 shows mass spectral data of fragment ions obtained by dissociating ions of m/z 154 at the ion trap portion.

FIG. 13 shows the mass spectral data (MS/MS) obtained by selecting the characteristic ions of m/z 154 shown in FIG. 11, capturing these ions at the ion trap portion 315, bombarding the ions with collision gas to dissociate the ions and generate fragment ions, and performing the mass spectrometry on the respective fragment ions with the ion detector 36. Information on not only the ions of m/z 154, but also the fragment ions of m/z 139, 83, 82, etc. appears in this mass spectral data, and this ion information corresponds to the structural factors of the molecules.

As a result of the qualitative analysis using the above library based on the mass spectral data of FIG. 13, the molecular structure is identified as Undecene (Undecene).

The sample analysis method according to this embodiment contains a step of displaying the thermal analysis data obtained in the thermal analysis step and the data obtained in the molecular structure analysis step on the same graph with the temperature set as a common variable. The thermal analysis data obtained in the thermal analysis step are thermogravimetry (TG) data and differential thermal analysis (DTA) data. The data obtained in the molecular structure analysis step are the mass spectral data shown in FIG. 12 or 13, for example. Information on the fragment ions corresponding to the structural factors of the component molecules contained in the gas evolved from the sample S appears in the mass spectral data.

As shown in FIG. 10, a graph displaying program for executing the graph display step is installed in the central control/processing device 50 in advance, and on the basis of this program, the central control/processing device 50 displays the thermal analysis data obtained in the thermal analysis step and the data obtained in the molecular structure analysis step on the same graph with the temperature set as a common variable.

Figure 14:
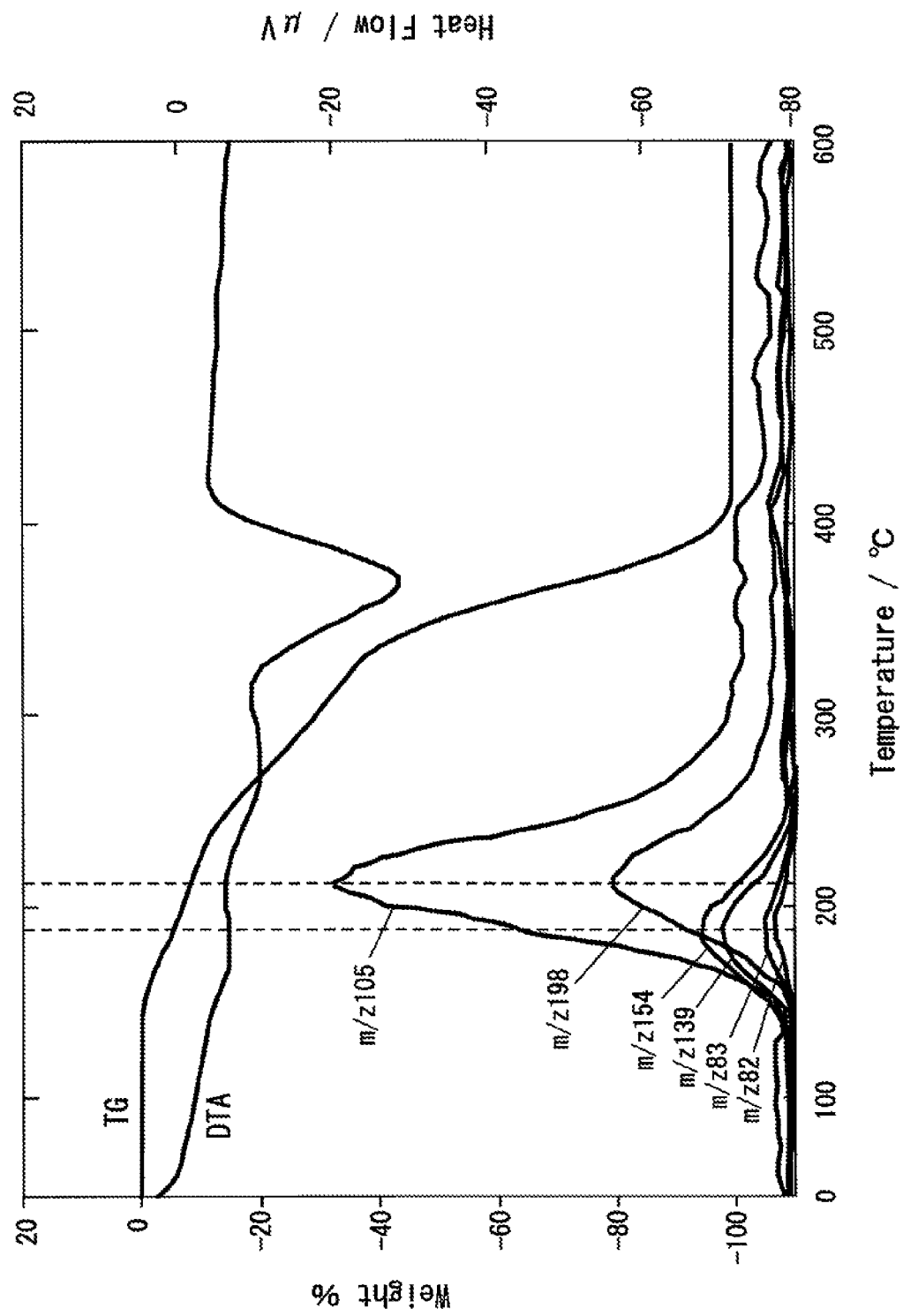
FIG. 14 is a diagram showing a graph on which both thermal analysis data obtained in a thermal analysis step and data obtained in a molecular structure analysis step are displayed with the temperature set as a common variable.

In FIG. 14, the thermogravimetry (TG) data, the differential thermal analysis (DTA) data, and thermograms (that is, thermograms of the respective fragment ions) with the temperature of the mass spectral data shown in FIG. 12 or 13 set as a variable are displayed on the same graph while the abscissa axis is set to the temperature.

This graph enables the identification analysis while the behavior of evolution of qualitatively analyzed gas components and the correlation of the thermal analysis curves can be clearly separated.

The present invention is not limited to the above embodiment, and various modifications and applications may be performed within the scope of the present invention described in "Claims". For example, in the above embodiment, the thermogravimetry (TG) and the differential thermal analysis. (PTA) are performed in the thermal analysis step. However, only the thermogravimetry (TG) may be performed, and the differential thermal analysis (DTA) may be omitted.

The invention claimed is:
1. A method for analysis of a sample comprising:
a temperature increasing step of increasing the temperature of a sample according to a predetermined temperature increasing program;
a thermal analysis step of performing thermal analysis on the sample;
a molecule ionization step of ionizing component molecules contained in gas evolved from the sample due to the temperature increase; and
a molecular structure analysis step of dissociating any selected ion out of molecular ions obtained in the molecule ionization step to generate fragment ions corresponding to structural factors of the molecule, and analyzing the structure of the molecule on the basis of the fragment ions, wherein the thermal analysis step, the molecule ionization step and the molecular structure analysis step are executed in parallel to the temperature increasing step, wherein thermal analysis data obtained in the thermal analysis step and data obtained in the molecular structure analysis step are displayed on the same graph with temperature set as a common variable, and wherein in the thermal analysis step, a mass variation of the sample due to the temperature increase of the sample is analyzed, the mass variation is displayed on a graph, and with respect to data obtained in the molecular structure analysis step, a thermogram of each of the generated fragment ions is displayed on the same graph as the mass variation.

2. The method for analysis of a sample according to claim 1, wherein the thermal analysis step is executed on the sample disposed in a sample chamber, the gas evolved from the sample due to the temperature increase is fed into an analysis chamber by a skimmer-type gas introducing interface, and the molecule ionization step and the molecular structure analysis step are executed in the analysis chamber.

3. The method for analysis of a sample according to claim 2, wherein the molecule ionization step and the molecular structure analysis step are executed by using an ion trap mass spectrometry instrument, and in the molecular structure analysis step, any selected ion out of molecular ions obtained in the molecule ionization step is captured, the captured ion is dissociated to generate fragment ions corresponding to the structural factors of the molecule, and the structure of the molecule is analyzed on the basis of the fragment ions.

4. The method for analysis of a sample according to claim 3, wherein in the molecule ionization step, component molecules contained in the gas evolved from the sample are irradiated with light to ionize the molecules.

5. A method for analysis of a sample comprising:
a temperature increasing step of increasing temperature of a sample according to a predetermined temperature increasing program;
a thermal analysis step of performing thermal analysis on the sample;
a molecule ionization step of ionizing component molecules contained in gas evolved from the sample due to the temperature increase of the sample; and
a molecular structure analysis step of dissociating any selected ion out of molecular ions obtained in the molecule ionization step to generate fragment ions corresponding to structural factors of the molecule, and analyzing the structure of the molecule on the basis of the fragment ions,
wherein the thermal analysis step is executed on the sample disposed in a sample chamber, the gas evolved from the sample due to the temperature increase is fed into an analysis chamber by a skimmer-type gas introducing interface, and the molecule ionization step and the molecular structure analysis step are executed in the analysis chamber, wherein the molecule ionization step and the molecular structure analysis step are executed by using an ion trap mass spectrometry instrument, wherein in the molecule ionization step, component molecules contained in the gas evolved from the sample are irradiated with light to ionize the molecules, wherein in the molecular structure analysis step, any selected ion out of molecular ions obtained in the molecule ionization step is captured, the captured ion is dissociated to generate fragment ions corresponding to the structural factors of the molecule, and the structure of the molecule is analyzed on the basis of the fragment ions, wherein the thermal analysis step, the molecule ionization step and the molecular structure analysis step are executed in parallel to the temperature increasing step, wherein thermal analysis data obtained in the thermal analysis step and data obtained in the molecular structure analysis step are displayed on the same graph with temperature set as a common variable, and wherein in the thermal analysis step, a mass variation of the sample due to the temperature increase of the sample is analyzed, the mass variation is displayed on a graph, and with respect to data obtained in the molecular structure analysis step, a thermogram of each of the generated fragment ions is displayed on the same graph as the mass variation.

* * * * *